US006765661B2

(12) United States Patent
Biel et al.

(10) Patent No.: US 6,765,661 B2
(45) Date of Patent: Jul. 20, 2004

(54) LENS INSPECTION (75) Inventors: Roger Biel, Frankfurt am Main (DE); Joachim Linkemann, Anhrensburg (DE); Livio Fornasiero, Hamburg (DE); Ingolf Braune, Gundelfingen (DE)

(73) Assignee: Novartis AG, Basel (CH)

( * ) Notice: Subject to any disclaimer, the term of this patent is extended or adjusted under 35 U.S.C. 154(b) by 161 days.

(21) Appl. No.: 10/091,819

(22) Filed: Mar. 6, 2002

(65) Prior Publication Data

US 2002/0163638 A1 Nov. 7, 2002

(30) Foreign Application Priority Data

Mar. 9, 2001 (EP) ............................................ 01105961

(51) Int. Cl.$^7$ ................................................ G01B 9/00
(52) U.S. Cl. ...................................................... 356/124
(58) Field of Search ................................ 356/124, 125, 356/126, 127, 239.1, 239.2, 435; 206/5.1

(56) References Cited

U.S. PATENT DOCUMENTS

| | | | |
|---|---|---|---|
| 3,268,068 A | 8/1966 | Grand ............................ | 206/5 |
| 3,556,636 A | 1/1971 | Roberts et al. ............... | 350/96 |
| 3,678,564 A | 7/1972 | Roberts et al. ............... | 29/419 |
| 3,861,808 A | 1/1975 | Halsey ........................ | 356/169 |
| 3,988,068 A | 10/1976 | Sprague ....................... | 356/124 |
| 4,009,948 A | 3/1977 | Boyan et al. ................ | 350/319 |
| 4,125,776 A | 11/1978 | Tosswill et al. ............. | 250/508 |
| 4,197,266 A | 4/1980 | Clark et al. .................. | 264/1 |
| 4,212,707 A | 7/1980 | Tosswill et al. .............. | 204/26 |
| 4,305,643 A | 12/1981 | Tosswill ...................... | 350/167 |

(List continued on next page.)

FOREIGN PATENT DOCUMENTS

| | | |
|---|---|---|
| DE | 3432002 A1 | 3/1986 |
| EP | 0 063 761 A1 | 4/1982 |
| EP | 60071933 | 4/1985 |
| EP | 0 249 799 B1 | 1/1992 |
| EP | 0 491 663 B1 | 1/1996 |
| EP | 0 604 178 | 2/1998 |
| GB | 1 536 497 | 12/1978 |
| GB | 2 058 393 | 4/1981 |
| GB | 2 226 272 | 6/1990 |
| JP | 55 134339 | 10/1980 |
| JP | 61096439 | 5/1986 |
| JP | 2 257007 | 10/1990 |
| JP | 4 305144 | 10/1992 |

OTHER PUBLICATIONS

European Search Report.
Electronic Imaging of Defects in Contact Lenses, Wilder & Davis, Vistakon (A Johnson & Johnson Co.), Jun. 1989, Scientifica.
Measurement of Spherical Aberrations Using a Solid–State Image Sensor, Suzuki, Ogura, & Ose, Applied Optics, vol. 18, No. 22, Nov. 15, 1979, pp. 3866–3871.

*Primary Examiner*—Frank G. Font
*Assistant Examiner*—Layla Lauchman
(74) *Attorney, Agent, or Firm*—Jian S. Zhou; Robert J. Gorman; R. Scott Meece (57) ABSTRACT

The invention enables more objective defect evaluation of ophthalmic lenses, especially contact lenses, to take place through the combination of the schlieren method with the transmitted light method, with the result that the advantages of these two different systems are combined. The schlieren method is in a position to illustrate the edge of a contact lens and its ruptures, in high contrast, for the CCD camera. Likewise, tears and surface defects can be made visible. Using the transmitted light method, the bubbles may be suitably prepared for the camera.

25 Claims, 6 Drawing Sheets

U.S. PATENT DOCUMENTS

| | | | |
|---|---|---|---|
| 4,320,977 A | 3/1982 | Matsumoto | 356/427 |
| 4,337,858 A | 7/1982 | Thomas et al. | 206/5.1 |
| 4,402,396 A | 9/1983 | Graham | 206/5.1 |
| 4,508,216 A | 4/1985 | Kelman | 206/5.1 |
| 4,526,445 A | 7/1985 | Wogoman | 350/534 |
| 4,534,645 A | 8/1985 | Nohda | 356/125 |
| 4,588,270 A | 5/1986 | Tamaki | 351/212 |
| 4,609,287 A | 9/1986 | Kohayakawa | 356/124 |
| 4,610,542 A | 9/1986 | Ringlien | 356/240 |
| 4,623,249 A | 11/1986 | Grant | 356/124 |
| 4,680,149 A | 7/1987 | Rawlings et al. | 264/2.1 |
| 4,691,820 A | 9/1987 | Martinez | 206/205 |
| 4,730,924 A | 3/1988 | Allard et al. | 356/125 |
| 4,736,130 A | 4/1988 | Puskas | 310/316 |
| 4,779,979 A | 10/1988 | Iwane | 356/125 |
| 4,782,946 A | 11/1988 | Pollak | 206/223 |
| 4,826,315 A | 5/1989 | Kohayakawa | 356/125 |
| 5,036,971 A | 8/1991 | Seden et al. | 206/5.1 |
| 5,080,839 A | 1/1992 | Kindt-Larsen | 264/2.6 |
| 5,086,397 A | 2/1992 | Schuster et al. | 364/468 |
| 5,099,987 A | 3/1992 | Bieri | 206/5.1 |
| 5,134,278 A | 7/1992 | Nelen | 250/223 |
| 5,143,660 A | 9/1992 | Hamilton et al. | 264/1.4 |
| 5,173,738 A | 12/1992 | Bieri | 356/124 |
| 5,231,460 A | 7/1993 | Kohayakawa | 356/125 |
| 5,303,023 A | 4/1994 | Portney et al. | 356/124.5 |
| 5,443,152 A | 8/1995 | Davis | 206/5.1 |
| 5,461,570 A | 10/1995 | Wang et al. | 364/468 |
| 5,500,732 A * | 3/1996 | Ebel et al. | 356/124 |
| 5,528,357 A | 6/1996 | Davis | 356/124 |
| 5,574,554 A | 11/1996 | Su et al. | 356/124 |
| 5,578,331 A | 11/1996 | Martin et al. | 425/445 |
| 5,633,504 A | 5/1997 | Collins et al. | 250/461.1 |
| 5,745,230 A | 4/1998 | Edwards et al. | 356/124 |
| 5,748,300 A | 5/1998 | Wilder et al. | 356/124 |
| 5,805,276 A | 9/1998 | Davis et al. | 356/124 |
| 5,812,254 A | 9/1998 | Ebel et al. | 356/124 |
| 5,818,573 A | 10/1998 | Lafferty et al. | 356/127 |
| 5,822,698 A | 10/1998 | Tang et al. | 455/447 |
| 5,828,446 A | 10/1998 | Davis | 356/124 |
| 5,995,213 A * | 11/1999 | Davis et al. | 356/124 |
| 6,047,082 A | 4/2000 | Rhody et al. | 382/141 |
| 6,134,342 A | 10/2000 | Doke et al. | 382/141 |
| 6,153,873 A | 11/2000 | Wolf | 250/208.1 |
| 6,201,600 B1 | 3/2001 | Sites et al. | 356/124 |
| 6,301,005 B1 * | 10/2001 | Epstein et al. | 356/124 |
| 6,577,387 B2 * | 6/2003 | Ross et al. | 356/124 |
| 6,606,150 B2 * | 8/2003 | Bickert et al. | 356/124 |

* cited by examiner

LENS INSPECTION

The invention relates to a device and a method for the automatic inspection of ophthalmic lenses, especially contact lenses, in an automatic lens manufacturing process.

The production of contact lenses using conventional methods, such as rotary processes for hard contact lenses and pouring processes for soft contact lenses in disposable plastic moulds is relatively expensive. As a rule, these contact lenses are used in a period of one year to one month. Technical advancement in recent years, however, has enabled contact lenses to be produced, which are worn only on one day and are replaced afterwards by new contact lenses. However, this has been made possible only through a high degree of automation of the production plants. Production of these contact lenses advantageously takes place using reusable mould halves, the matrix and the patrix, which normally consist of glass or quartz. Between these mould halves is a hollow cavity, which corresponds to the subsequent contact lens shape. Before closing the mould halves, a polymer solution is measured into the matrix. UV light is radiated over the upper mould half, which leads to crosslinking of the lens material. Subsequently, the lens is removed from the mould half with suction grips and is placed in the pack.

In order to assure constant quality of the contact lenses, provisions are in place for automatic inspection of the contact lenses using industrial image processing methods. In image processing, the lenses are tested both in the mould halves and at the vacuum grips. An image processing method of this kind is described for example in EP patent 491663. Of course, not all defective contact lenses can be detected by this type of inspection, or nominal defects are established, such as bubbles formed by water spillages, which however illustrate artefacts. By having to sort out the perfect lenses, the yield is reduced, which has a negative effect on balancing the costs.

The invention is based on the problem of providing an inspection device and an inspection method, which recognises the defective lenses with a high degree of reliability, but does not falsely sort out perfect lenses. In particular, the image-processing system should carry out a complete examination of the contact lenses for accuracy of size, surface defects, tears, peripheral ruptures and inclusions such as bubbles and foreign bodies.

The invention solves this problem with the features of claim 1 and claim 21. As far as further essential developments of the equipment according to the invention and of the process are concerned, reference is made to the dependent claims.

Through the combination of the schlieren method and the transmitted light process, the advantages of both systems can be linked, so that defects can be evaluated more objectively. The schlieren method is in a position to illustrate the edge and its ruptures in high contrast for the CCD camera. Likewise, tears and surface defects can be made visible. With the transmitted light process, the bubbles can be appropriately prepared for the camera, so that defects can all be recognised in terms of the required test criteria.

Further details and advantages of the invention may be seen from the description that follows and the drawing. In the drawing.

In automatic quality control, the accuracy of size, the shape and the surface of the contact lens should be checked. The edge of the contact lenses should be tested for ruptures and tears, and the surface over the whole contact lens should be tested for bubbles, inclusions and surface defects. According to the invention, the principle points of quality testing are in particular control of the edges and finding bubbles.

Further quality criteria of a contact lens are its geometric properties such as accuracy of size and roundness. The shape of a contact lens can be approximately described as part of a ball cup. If the prescribed measurements are not adhered to, in the actual manufacturing process an error may occur, which has a negative effect on the quality of the contact lens. The lens diameter may be determined from the outer edges of the contact lens. By determining the maximum and minimum lens diameter, a measure of the eccentricity of the contact lens can be deduced. The roundness of the lens results from the contour of the edge.

In addition, all contact lenses are to be inspected for damage to the outer edges. This damage frequently occurs in the form of ruptures or tears. A peripheral rupture is described as missing material on the periphery of the contact lens. A small tear in the contact lens can rapidly lead to a continuation of the tear and complete destruction of the contact lens. Then, parts of the contact lens can easily become trapped between the eye and the eye lids and are very difficult to remove. Tears frequently progress from the outer periphery to the inside of the contact lens. They are usually easy to see, as the halves of the tear split away from one another. However, it is also known that when the halves of the tear lie next to one another, the tear can barely be seen optically owing to the negligible difference in refractive index of water and polymer, as the scattering properties of the edge of the tear are lost.

Circular defects may occur in the internal region of the contact lens. These defects arise during production, due to the inclusion of small air bubbles or foreign bodies in the polymer solution.

Surface defects are distinguished by linear and areal defects. They are noted for their rough surface structure. The defective area and the spread are used for evaluation purposes.

Figure 1:
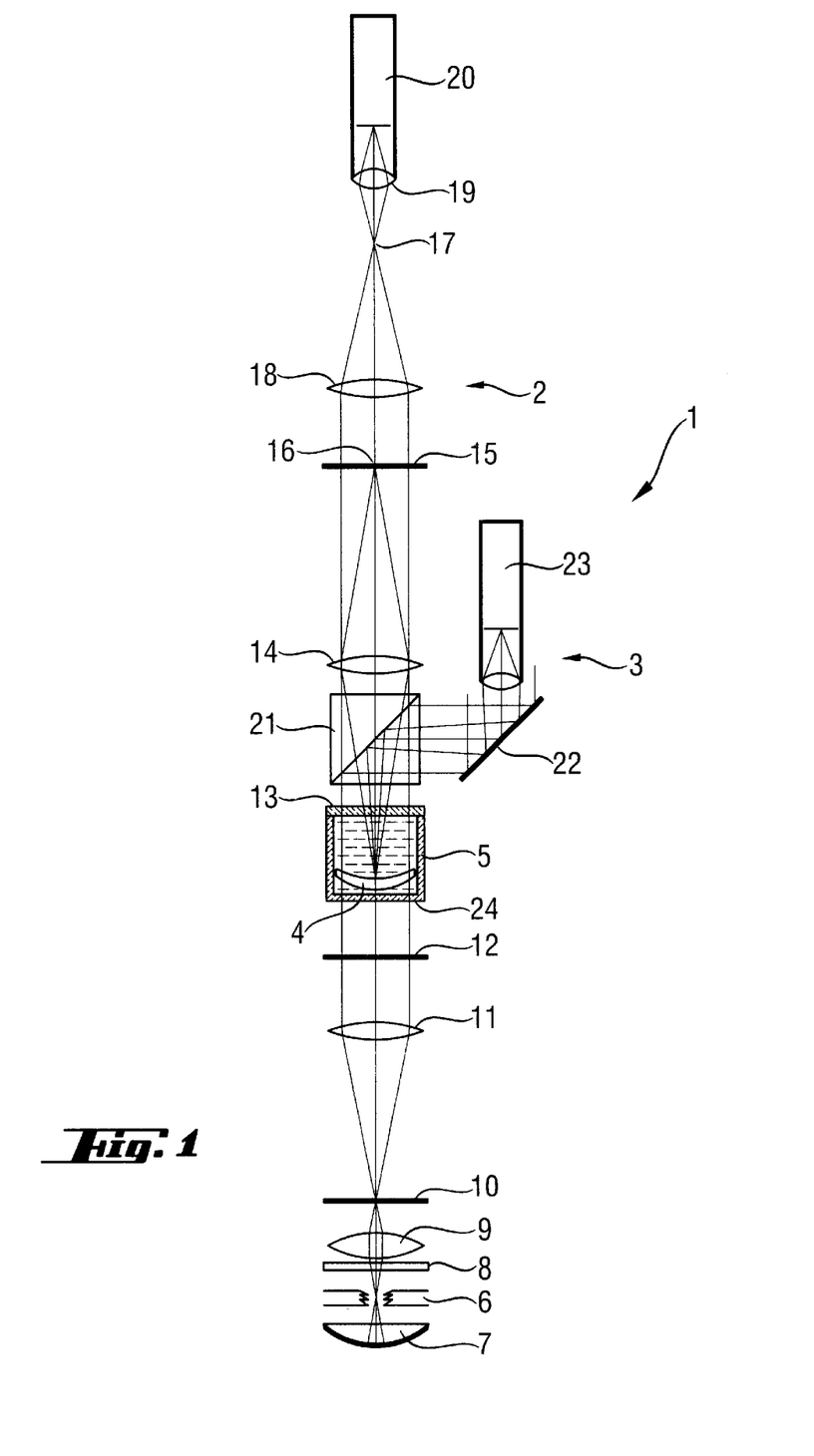
FIG. 1 shows a schematic illustration of an inspection device according to the invention.

The inspection device 1 according to the invention illustrated in FIG. 1 consists of a dark-field observation 2 and a bright-field observation 3. The contact lens 4 which is preferably a soft one is held in a container 5. The container 5 is filled with water or a similar test liquid. However, this places particular demands on the inspection system, since the contact lens 4 itself has a water content of approximately 69%. Therefore, the refractive index of the contact lenses $n(K)=1.382$ is very close to the refractive index of water $n(W)=1.333$, which means that the contact lens 4 can only be seen with great difficulty in water. Of course, by examining in water, artificial defects, so-called artefacts, especially bubbles caused by water spillages during production, can be avoided, and the scrapping of lenses which have been erroneously detected as defective can be avoided. In addition, by examining in water, it is possible to ensure that the testing environment is free of dust and fluff. When calculating the imaging properties of the inspection device, the height of the constructed container 5 must be taken into consideration. By replacing air in the beam with a medium having a higher refractive index, such as glass or liquid, the imaging properties are modified and, correspondingly, the aberrations, which have to be minimised.

A halogen lamp 6 is preferably used as the light source to illuminate the contact lens 4. To increase the output of light, a concave mirror 7 is used. The light reflected by the halogen lamp 6 and the concave mirror 7 is focussed onto the input diaphragm 10 by a heat filter 8 and a biconvex lens 9. This diaphragm 10 lies in the focus point of a further lens 11, so that the light emanating from the halogen lamp 6 is collimated and parallel light is present in the examining zone. It is also possible for an interference filter 12 to be additionally used behind the lens 11, in order to substantially increase the length of coherence of the light emanating from the halogen lamp 6. The contact lens 4 is located in the cuvette 5 introduced into the illumination path, the cuvette preferably being closed off by a flat glass sheet 13. The cuvette 5 should be closed, in order to enable crossing points of the individual optical media to be cleanly defined. If the liquid is not covered, vibration or jolting may, for example, produce non-reproducible, partly chaotic deformation of the wave fronts. The resulting image can be compared with "light refraction" on the bottom of a swimming pool.

The contact lens 4 is subsequently observed in a dark field or bright field. For the illumination beam and the observation beams, achromatic lenses were preferably used, in order to avoid aberrations.

For the dark-field observation, an image of the contact lens to be tested is formed on an intermediate image via a 4f set-up and then taken with a lens from a ½" S/W camera. For soft contact lenses, the greatest scattering amplitude occurs when there are only small deviations of the scattering angle from the direction of the radiated light. Therefore, observation in a dark field is preferably carried out under a small angle. The contact lens 4 is located in the focal plane of a convex lens 14. High grade optical equipment with a free diameter of 48 mm is advantageously used, in order to film the whole contact lens 4 in any position on the bottom of the cuvette 5. To do this, achromatic lenses with a diameter of 50 mm are suitably employed. In order to enable a compact structural unit to be used, achromatic lenses with a focal length of f=100 mm are advantageously used. In the focal plane 15 on the other side of the lens 14, hereinafter called the filter plane, is the optical Fourier transformation to the focal plane, which contains the contact lens 4. The zero order of the Fourier transformations is the illumination used. This is a conjugated plane to the input diaphragm 10 of the illumination. Through the diameter of a diaphragm 16 present in the filter plane 15, low and high spatial frequencies can be filtered out without point-focally affecting the actual image. What is important is that the imaging properties of the contact lens 4 can be disregarded. Through a subsequent back-transformation, finally a real image of the contact lens 4 is again obtained, which had previously been filtered. Since the diaphragm 16 in the filter plane 15 scatters the illuminating light, the term beam stop is used hereinafter. This method, which was introduced by A. Toepler to examine lenses, may be found in literature under the name schlieren method. Schlieren systems are especially useful for examinations where slight changes of the refractive index become visible. The direction of the light rays are easily changed by slight changes to the refractive index. It is just this behaviour that is used when inspecting the contact lens. The beam stop 16 in the filter plane 15 should advantageously be of larger diameter than the input diaphragm 10, so that the illuminating part of the beam is fully scattered by the imaging properties of the contact lens 4 despite deviations in the illuminating beam. Of course, the beam stop 16 should not be too large, since otherwise too many low frequency parts are filtered out at this point. Finally, the deviation of the scattered beam is only small against the direction of the beam. Using computer-assisted simulation of the path of the beam and the confirmation from the experiments, with an input diaphragm 10 of 1 mm, the size of the beam stop 16 is advantageously 2–3 mm.

In optics, the so-called spot function describes the different sizes of images of infinitesimally small points which are localised on the object. In order to obtain an image which corresponds to the resolution of a CCD sensor, they are compared with the size of one pixel (ca. 10 $\mu$m×10 $\mu$m). Within one pixel, all appearing photons (with infinite probability) are integrated. Therefore, the spot function should always lie within a size given by the dimensions of a pixel. In particular, with an intermediate image 17 through a lens 18, as is indicated in the beam in FIG. 1, the spot function is smaller than the pixel size. The intermediate image 17 is then taken by a lens 19 of a camera 20.

The observation results on a dark field show that the edge, and therefore also defects in the edge, such as ruptures can be illustrated very well. In principle, surface defects can be discerned in dependence on the scattering behaviour of a rough surface. However, linear surface defects are less easily recognised.

Bubbles are easily recognised, but cannot be exactly specified according to their size, i.e. a small bubble appears brighter and larger throughout than a large bubble. The cause lies in the non-linear scattering behaviour of the bubbles. If, for example, a contact lens contains two little bubbles which are each smaller than 50 $\mu$m, this still counts as acceptable. It is therefore necessary to portray the bubbles in proportion to their size.

Therefore, according to the invention, the path of the beam after the cuvette 5 is divided and the contact lens 4 is additionally examined in transmitted light. To do so, in the path of the beam after the cuvette 5, a beam-dividing cube 21 is inserted, so that the view over the contact lens 4 is divided. One beam is that formerly of the schlieren optics 2 and the other beam is that given in transmitted light 3. The additional glass unit 21 must be taken into consideration when calculating the imaging properties. The diffracted beam is again reflected by a mirror 22, in order to optimise the size, but also to equalise the image orientation. Through the small residual divergence, sufficient sharpness in depth can be attained. The image of the contact lens 4 is then taken by a camera 23.

Examination results show that the bubbles can be depicted to scale with the assistance of the transmitted light process. Thus, using this combination arrangement, all defects in the contact lens which should be detected are illustrated very well.

All the optical elements of the structure and the contact lens should ideally lie in one optical axis. The demand for high positioning accuracy of the contact lens on the cuvette base 24 stems from this. In addition, good observation of the contact lens 4 is only provided if contact of the contact lens 4 with the edge of the cuvette 5 is avoided. So that the contact lens 4 can float independently in the centre of the cuvette 5, the base 24 may be advantageously shaped as a watch glass. However, the watch glass is an optical element of the structure and influences the imaging properties of the whole structure. The consequences thereof must be heeded. Due to its curve and its refractive index other than the surrounding fluid, the watch-glass dish likewise has imaging properties. These refract the parallelity of the illuminating light. This is noticeable in such manner that the beam stop 16 has to be enlarged. If, however, the beam stop 16 is too large, then too little scattered light from the contact lens 4 passes the beam stop 16. In other words, too many low spatial frequencies are suppressed. The greater the convexing of the watch-glass dish, the greater its refraction. It has been shown that a radius of curvature of R=50 mm has proved to be advantageous.

The test equipment uses for evaluation both the light-scattering properties of the defect features and the transmission properties of the defect features. However, these properties possess not only defects and structures of the contact lens, but also foreign bodies in the test liquid. Therefore, very high demands are placed on the cleanliness of the cuvette 5 in respect of dirt and fluff. In order to detect defects which have a negative effect on the quality of the contact lens, a minimum resolution of 50 $\mu$m is necessary to recognise the smallest defects. However, as a result of the high resolution of the optics, not only the defects, but also all the foreign bodies on the contact lens and in the test liquid are visible. This includes, in particular, dust particles and fluff. With a square-shaped cuvette 5, the smallest particles are deposited in the corners and edges. However, these are likewise very visible with a high-resolution inspection device. Dust particles, which are present in the liquid, scratches and dirt on the bottom or cover of the cuvette 5, and the like, are similarly displayed by the schlieren method. Dust particles form an almost isotropic scattering centre, so that they can appear considerably brighter than a scattering centre which scatters very anisotropically. It is therefore only partly possible to distinguish foreign bodies and defects on the contact lens. Fluff can be detected by its linear structure. However, tears or linear surface defects similarly possess this feature. Dust particles and bubbles in the contact lens are represented by small round regions in the image. It is not possible to unequivocally examine bubbles and dust particles. Of course, only the scattering centres found around the contact lens 4 make a detrimental contribution to the image. For this reason, it is important to clean the test liquid. It is advantageous for cleaning of the test liquid to take place permanently, since it is almost certain that foreign bodies will appear during continuous operation. This can be ensured by having a permanent cleaning process of the test liquid through filters, or by continuously replacing the test liquid.

Equally high demands as on the test liquid are placed on the cuvette bottom 24, since this is a component of the optical testing area in respect of the depth of focus. The cuvette bottom 24 should not have any streaks in the glass, nor scratches or particles of dirt on the surface. These demands may be fulfilled by careful handling of the cuvettes 5 and by permanently cleaning. After each testing procedure, the any particles of dirt or remains of contact lenses in the cuvette 5 should be cleaned.

For optimum illumination and imaging of the contact lens 4, its position in the cuvette 5 while the image is being taken is of crucial importance. The shift should preferably not exceed 0.5 mm in the x and y coordinates. If these values are exceeded, the resolving power is reduced. This leads to errors in the image of the edge and to inadequate control in the periphery. The z coordinate is restricted by the depth of focus of the schlieren optics and the scope of the telecentric optics. This should preferably not exceed 0.5 mm.

By tilting, the an ellipse-shaped image of the contact lens is made, subject to the projection. However, in the plan view, this cannot be distinguished from a non-round contact lens. Since the roundness is a crucial test criteria, the tilting must be excluded.

After placing in the cuvette, the contact lens must float in a central position. The lens must remain there for two reasons. First of all, a precise trigger point is defined for the optimum location for taking a picture under optimum conditions, and secondly, a defined access point is created for removing the contact lens. Any self-movement must be restricted to the floating process. After this, the contact lens must not undertake any further movement in the cuvette. The contact lens must be prevented from making contact with the side wall of the cuvette. Although the edge can be detected as such, any evaluation of ruptures or tears cannot be reliably made, as the side wall of the cuvette can mask these defects in the image.

Before an image can be automatically processed by computer, this image must be present in the memory of the computer. To do this, an area of an object scene is observed by an electronic camera and the camera image is treansferred to the memory by an appropriate interface card. An object scene can be defined as a continuous image signal of a function of two constant local variables x and y. Using an optical system, a section of this scene is illustrated, in its image plane, on a two-dimensional CCD sensor of a camera. This area, which is of interest for further operations, is called the image. The optical system changes the image through its imaging properties, which may be described, by way of example, by their transfer function. The image is now stored as a constant continuous signal on the CCD sensor, through which it is scanned locally. The result of this operational step is a continuous picture signal of two distinct local variables. Then, quantisation of the picture signal by the AD converter follows. Now there is a digital picture signal as a function of two distinct local variables, which is placed in the memory. Such a matrix of distinct elements, with the line index i and the column index j, is called a digital image. The elements of this matrix are called a picture element or pixel. One pixel is described by its position (i,j) and its brightness value, the grey value (G={0, 1, . . . 255}).

$$g(i,j) \in G$$

A digital image can be divided into two principal areas of importance, the foreground and the background. The background contains no relevant information, for which reason it remains more or less unnoticed. The foreground is described as all picture areas which undergo further processing. This includes structures, objects and regions, whose features prepare the foundation for the decision made in testing.

The objects are described as picture areas in the foreground, which may be described by a closed curve path and are delimited from their surroundings by an object edge. Pixels of the object edge are distinguished from the background by a difference in their grey value. The enclosed picture region may assume the same or a different grey value from the background.

Because objects have been through about their delimitation from the background and from one another, in the foreground they illustrate separate picture regions. However, these are still two-dimensional images with a substantial amount of data. It is therefore the aim of further operations to reduce the amount of data used to describe the objects and their properties to a few characterising quantities, the characteristics.

Such characteristics, also called primary characteristics, may be e.g. circumference, area, average grey value or the maximum extent of the x and y axis. They prepare metrics for the measurement of object properties. Characteristics thus form the foundation for classification, i.e. a correlation of importance.

On the basis of this definition, the contact lens is an object, the edge of which stand out from the background. The contact lens edge itself must be checked for defects, such as tears and ruptures. Testing is possible by tracking the edge and comparing it with a defined shape. If the edge deviates from this, for each part region a defective area is formed from the sum of all deviating image elements as a defective area. For detailed analysis of the contact lens edge, processes for analysing shape and evaluating the peripheral properties are used.

After the edge of the contact lens has been identified, an inner region is fixed, whose area is enclosed by the edge. An analysis is now made of punctiform and areal deviations of the grey value and compared with the general background grey value. This method, which takes advantage of the gradients of the grey value curve, thus takes into account local variations in the intensity of the background.

Using a procedure of this kind, objects such as inclusions, surface defects and other deviations may be recognised, since they are delimited from the background by their edges. In part, surface defects have marked edge characteristics. They are however distinguished from the defect-free background by their texture. Characteristics used to describe discovered defective objects are grey value, contour, off size and area.

After detecting deviations on the lens edge and in the inner area, the defective objects must be classified in order to make a decision on the test. The defective area, number of defects, off size, shape and position are used to describe the type of defect and as a criterion for rejection.

It is expedient to employ a multi-stage classification process, since in the first stage of classification, the importance must be correlated, and only then can a comparison be made with the rejection criteria. For example, a bubble has a smaller defective area than a surface defect. In the second stage of classification, a decision as to whether the defective object should be further processed or may be tolerated in the product is made on the basis of individual rejection criteria. In the further processing, defects are differentiated into individual defects and groups defects. Individual defects must immediately lead to a decision to reject them, because of their large deviation of individual parameters from the maximum tolerance. Group defects are defined through a maximum number of smaller defects. Here, single or many defects are tolerated. It is only when a maximum number has been exceeded that the decision to reject is made.

Figure 2:
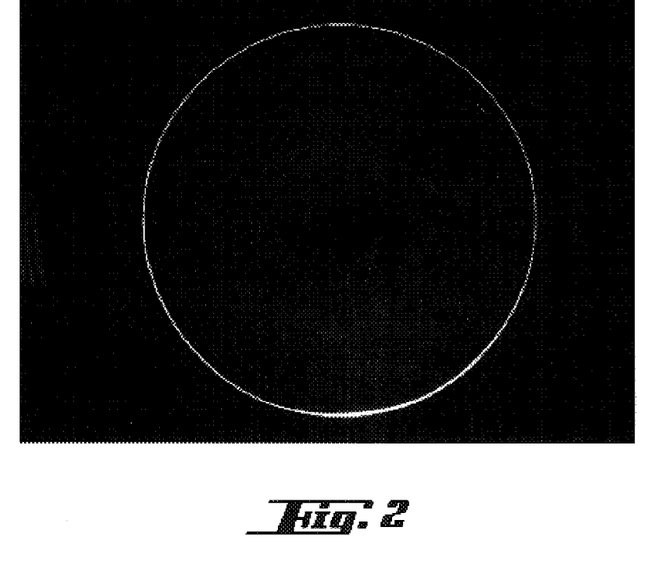
FIG. 2 shows an image of a perfect contact lens on a dark field.
Figure 3:
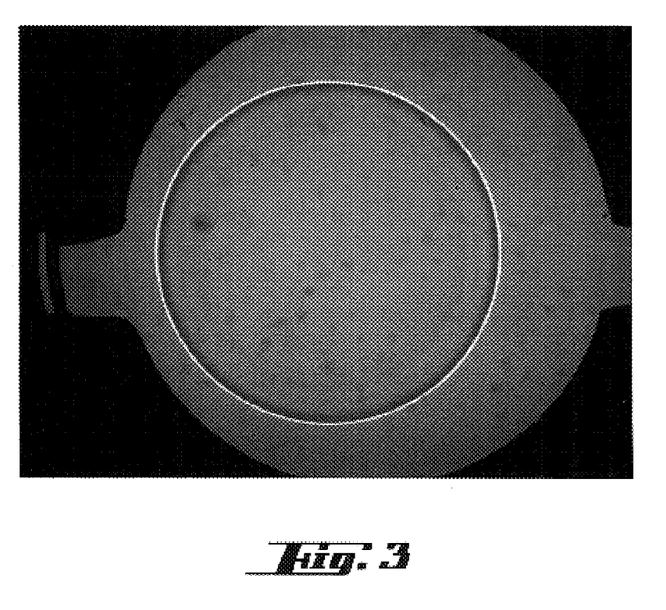
FIG. 3 shows an image of a perfect contact lens in transmitted light.

FIGS. 2 and 3 show images of a perfect contact lens. The contact lens is defined by its edge, which is distinguished from its surroundings by a high contrast. The inner area is homogeneous and does not contain any further objects. FIG. 2 was taken using schlieren optics and FIG. 3 with by the transmitted light method. Using the schlieren technique, the edge of a contact lens offers an image with a very high contrast over the background. As can be discerned from FIG. 3, the edge can also be checked by the transmitted light method.

Figure 4:
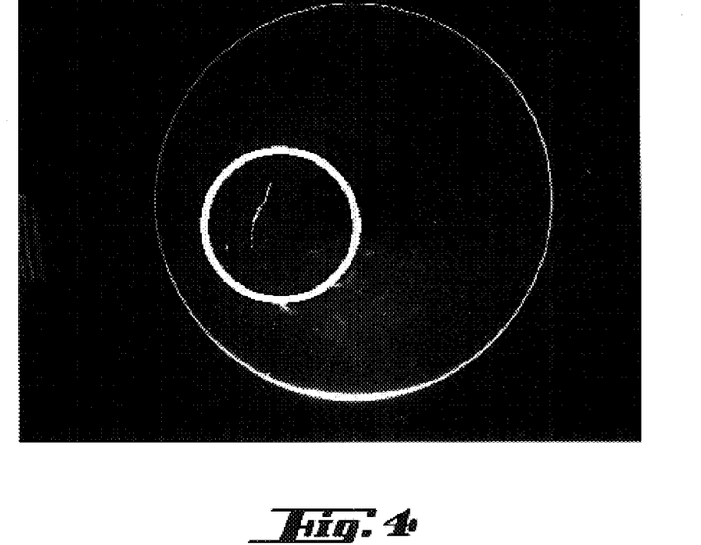
FIG. 4 shows an image of a contact lens with a tear on a dark field.
Figure 5:
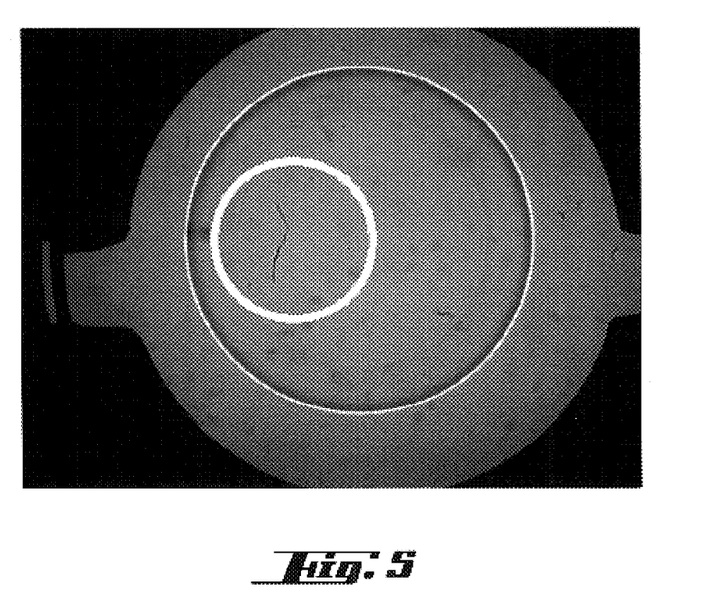
FIG. 5 shows an image of a contact lens with a tear in transmitted light.
Figure 6:
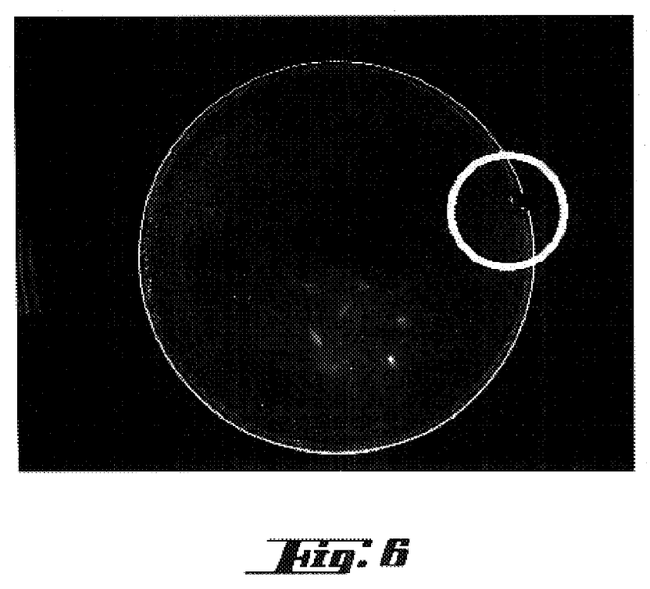
FIG. 6 shows an image of a contact lens with a peripheral rupture on a dark field.
Figure 7:
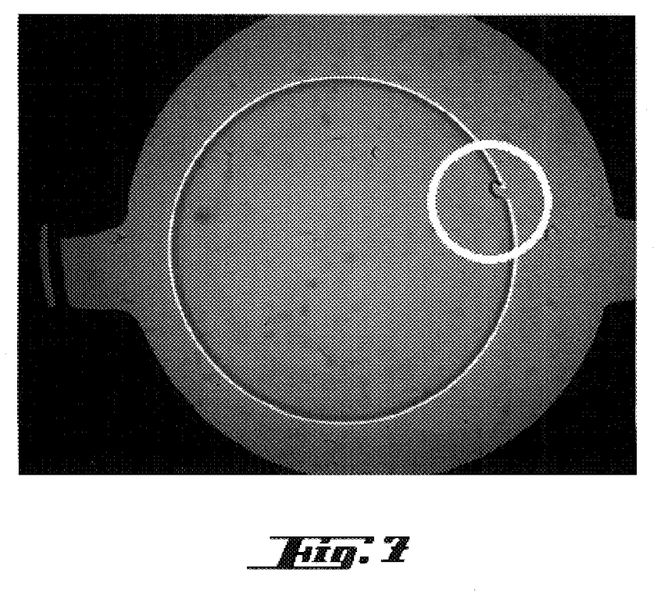
FIG. 7 shows an image of a contact lens with a peripheral rupture in transmitted light.

An image of tears can also be made by the transmitted light method, as can be inferred from FIGS. 4 and 5. To recognise defects, both images, i.e. the image on a dark field and the image in transmitted light, are combined to give optimum results. The check the contact lens edge, the edge is tracked over one revolution of the whole lens FIGS. 6 and 7 illustrate a lens with a ruptured edge. Ruptures or tears represent defects in the course of the arc, and can be evaluated by their off sizes and defective areas. Both methods use comparisons to a reference sample, in order to recognise deviations. Peripheral defects are clearly classified as important because of their position and their appearance, which simplifies the first classification step. Afterwards, it is possible to evaluate the defect parameters.

Figure 8:
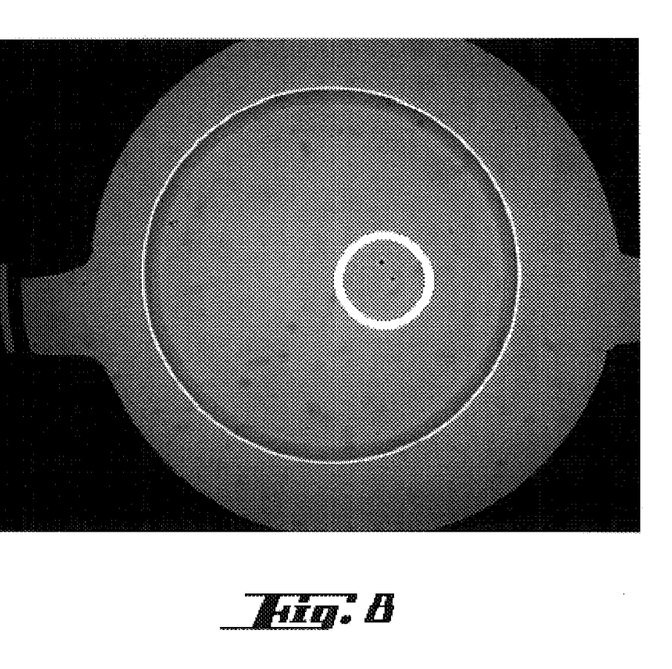
FIG. 8 shows an image of a contact lens with bubbles and inclusions in transmitted light.

As is evident from FIG. 8, inclusions or bubbles are portrayed as dark points or small circles with a dark edge shown on the light background. The diameter, shape and number are used to determine the basis of these characteristics.

Figure 9:
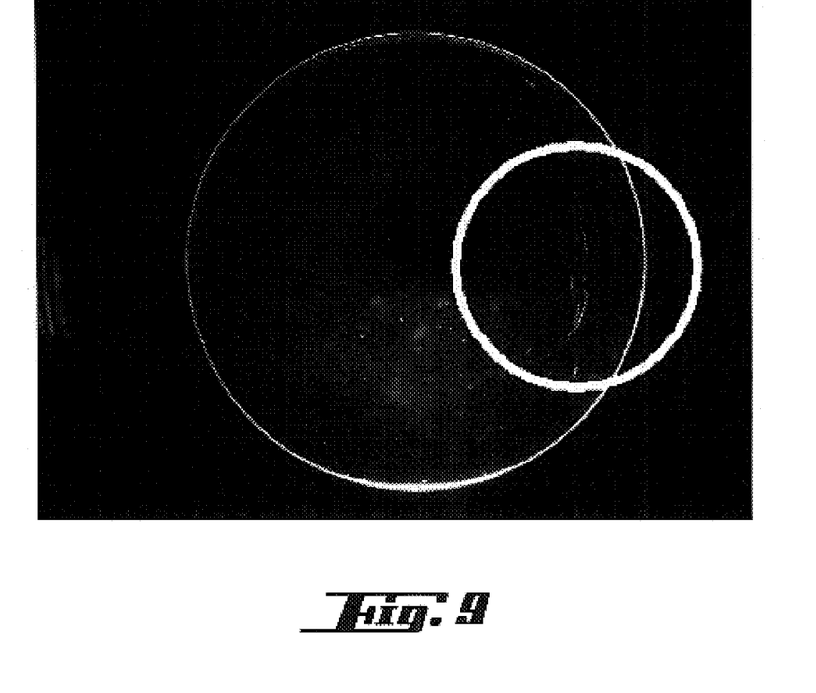
FIG. 9 shows an image of a contact lens with a surface defects on a dark field.

Surface defects may be recognised by their light-scattering properties. To recognise defective regions, diffuse linear or areal regions are used, which can be evaluated by their spread. In the case of linear surface defected, both methods achieve approximately the same result. This type of defect is classified by its position within the lens, its linear length and the defining rectangle. However, areal surface defects can only be recognised by schlieren optics. FIG. 9 illustrates a contact lens with surface defects on a dark field.

In all, the invention enables more objective defect evaluation to take place through the combination of the schlieren method with the transmitted light method, with the result that the advantages of these two different systems are combined. The schlieren method is in a position to illustrate the edge and its ruptures in high contrast for the CCD camera. Likewise, tears and surface defects can be made visible. With the transmitted light process, the bubbles can be suitably prepared for the camera, so that defects can all be recognised in terms of the required test criteria.

We claim:

1. A device for the automatic inspection of ophthalmic lenses, comprising: a light source providing an illuminating light to illuminate an ophthalmic lens to be inspected; a holding device for the ophthalmic lens, wherein the holding device is located in the path of the illuminating light so that the ophthalmic lens is observed in an observation beam consisting of a dark-field observation beam and a bright-field observation beam; a first imaging device located in to path of the dark field observation beam for taking a dark-field image of the ophthalmic lens on a dark-field; a second imaging device located in the path of a bright-field observation beam for taking a bright-field image of the ophthalmic lens on a bright field; and an image analysing equipment, wherein both the dark-field image and the bright-field images are taken simultaneously and then transmitted to to image analyzing equipment where they are processed and analyzed for defect evaluation of the ophthalmic lens.

2. Inspection device according to claim 1, in which a beam divider (21) is provided to divide the observation beam into dark-field observation (2) and bright-field observation (3).

3. Inspection device according to claim 1, in which the lens (4) is examined in transmission.

4. Inspection device according to claim 2, in which the lens (4) is held in a container (5).

5. Inspection device according to claim 4, in which the container (5) is filled with water or a similar test liquid.

6. Inspection device according to claim 5, in which the container (5) is covered by a glass plate (13).

7. Inspection device according to claim 2, in which a convex lens (14) is provided for the dark-field observation (2), and the lens (4) is located in one of the focal planes of this convex lens (14).

8. Inspection device according to claim 7, in which an achromatic lens with a free diameter of 48 mm and a focal length of 100 mm is used as the convex lens (14).

9. Inspection device according to claim 7, in which a diaphragm (16) is provided as a beam stop in the second focal plane of the lens (14).

10. Inspection device according to claim 9, in which the size of the input diaphragm (10) is 0.7 to 1.4 mm and the size of the diaphragm (16) lies in the range of 1.6 to 4 mm.

11. Inspection device according to claim 7, in which the beam-dividing cube (21) is provided between the container (5) and the convex lens (14).

12. Inspection device according to claim 1, in which the lens (4) is illuminated with parallel light.

13. Inspection device according to claim 12, in which a halogen lamp (6) is provided as the light source.

14. Inspection device according to claim 13, in which a concave mirror (7) is used to reflect light coming from the light source.

15. Inspection device according to claim 14, in which the light coming from the light source is focussed onto a diaphragm (10) by a biconvex lens (9).

16. Inspection device according to claim 15, in which a heat filter (8) is provided between the halogen lamp (6) and the diaphragm (10).

17. Inspection device according to claim 16, in which the diaphragm (10) is in the centre of a further lens (11).

18. Inspection device according to claim 17, in which all optical elements of the illuminating beam (7, 6, 8, 9, 10, 11) and the dark-field observation (2) lie on one optical axis.

19. Inspection device according to claim 9, in which a second lens (18) is provided behind the diaphragm (16) to produce an intermediate image (17).

20. Inspection device according to claim 1, in which a CCD camera is provided as the imaging device.

21. Process for inspecting an ophthalmic lens or a contact lens (4), whereby the lens is illuminated, an image of the lens is taken by an imaging device and is subsequently analysed by image analysing equipment by automatic image-processing methods, characterised in that the lens is observed on a dark field (2) and a bright field (3) simultaneously and the images of the lens on a dark field and bright field are simultaneously taken by the imaging device and transmitted to the image-processing unit.

22. Process according to claim 21, in which a common observation beam is provided, which is divided by a beam divider into the dark-field observation beam and the bright-field observation beam.

23. Process according to claim 21, in which the lens is illuminated in transmission with parallel light.

24. Process according to claim 21, in which the lens is located in a container (5) filled with water or a test liquid.

25. Process according to claim 21, in which the beam is divided behind the container (8).

* * * * *